US011712678B2

(12) United States Patent
Kim et al.

(10) Patent No.: US 11,712,678 B2
(45) Date of Patent: Aug. 1, 2023

(54) PREPARATION METHOD OF SUPER ABSORBENT POLYMER

(71) Applicant: LG Chem, Ltd., Seoul (KR)

(72) Inventors: Dong Hyun Kim, Daejeon (KR); Tae Bin Ahn, Daejeon (KR); Jun Wye Lee, Daejeon (KR); Chang Sun Han, Daejeon (KR)

(73) Assignee: LG Chem, Ltd.

(*) Notice: Subject to any disclaimer, the term of this patent is extended or adjusted under 35 U.S.C. 154(b) by 1353 days.

(21) Appl. No.: 16/086,244

(22) PCT Filed: Dec. 26, 2017

(86) PCT No.: PCT/KR2017/015485
§ 371 (c)(1),
(2) Date: Sep. 18, 2018

(87) PCT Pub. No.: WO2018/139768
PCT Pub. Date: Aug. 2, 2018

(65) Prior Publication Data
US 2020/0164344 A1 May 28, 2020

(30) Foreign Application Priority Data
Jan. 24, 2017 (KR) .................. 10-2017-0011253

(51) Int. Cl.
C08J 3/24 (2006.01)
A61L 15/24 (2006.01)
C08F 220/06 (2006.01)
B01J 20/26 (2006.01)
A61L 15/60 (2006.01)
B01J 20/28 (2006.01)
B01J 20/30 (2006.01)
B29B 9/06 (2006.01)
B29K 33/00 (2006.01)
B29K 105/24 (2006.01)
C08J 9/04 (2006.01)
C08J 3/12 (2006.01)

(52) U.S. Cl.
CPC ............ B01J 20/267 (2013.01); A61L 15/24 (2013.01); A61L 15/60 (2013.01); B01J 20/28004 (2013.01); B01J 20/28016 (2013.01); B01J 20/3007 (2013.01); B01J 20/3085 (2013.01); B29B 9/06 (2013.01); C08F 220/06 (2013.01); B29K 2033/08 (2013.01); B29K 2105/24 (2013.01); B29K 2995/0068 (2013.01); C08F 2800/20 (2013.01); C08F 2810/20 (2013.01); C08J 3/12 (2013.01); C08J 3/24 (2013.01); C08J 9/04 (2013.01)

(58) Field of Classification Search
CPC ........ C08F 20/04; C08F 20/06; C08F 220/04; C08F 220/06; B01J 20/267; B01J 20/28004; C08J 3/12
See application file for complete search history.

(56) References Cited

U.S. PATENT DOCUMENTS

| 5,338,766 | A | 8/1994 | Phan et al. |
| 5,562,646 | A | 10/1996 | Goldman et al. |
| 8,791,210 | B2* | 7/2014 | Sakamoto ............ C08F 220/06 526/318.41 |
| 9,447,203 | B2* | 9/2016 | Machida ............... B01J 20/3007 |
| 9,700,873 | B2* | 7/2017 | Lee ......................... C08J 3/005 |
| 10,335,768 | B2* | 7/2019 | Ahn ....................... B01J 20/267 |
| 10,406,256 | B2* | 9/2019 | Torii ......................... B29B 9/12 |
| 10,450,425 | B2* | 10/2019 | Nam ..................... B02C 18/365 |
| 10,603,653 | B2* | 3/2020 | Tada ..................... B01J 20/103 |
| 10,821,418 | B2* | 11/2020 | Nam ....................... C08J 3/245 |
| 10,822,441 | B2* | 11/2020 | Lee .................... B01J 20/28004 |
| 11,000,829 | B2* | 5/2021 | Ahn ........................ C08J 3/245 |
| 11,498,050 | B2* | 11/2022 | Kim ........................ C08J 3/122 |
| 2004/0249120 | A1 | 12/2004 | Nagasawa et al. |
| 2007/0207924 | A1 | 9/2007 | Ikeuchi et al. |
| 2013/0026412 | A1 | 1/2013 | Machida et al. |
| 2014/0312273 | A1 | 10/2014 | Wattebled et al. |
| 2015/0376318 | A1 | 12/2015 | Haag et al. |
| 2016/0199529 | A1 | 7/2016 | Torii et al. |
| 2016/0207226 | A1 | 7/2016 | Torii et al. |
| 2016/0311985 | A1* | 10/2016 | Jung ....................... C08J 3/245 |
| 2016/0332141 | A1 | 11/2016 | Machida et al. |
| 2017/0065739 | A1* | 3/2017 | Braun ................... B01J 20/267 |
| 2017/0216817 | A1 | 8/2017 | Torii et al. |
| 2018/0094131 | A1 | 4/2018 | Tanaka et al. |
| 2018/0185819 | A1 | 7/2018 | Ahn et al. |
| 2018/0298132 | A1* | 10/2018 | Yorino ........................ C08J 3/24 |

FOREIGN PATENT DOCUMENTS

| EP | 2399944 A1 | 12/2011 |
| EP | 2535027 A1 | 12/2012 |
| EP | 2557095 A1 | 2/2013 |
| EP | 2565219 A1 | 3/2013 |

(Continued)

OTHER PUBLICATIONS

International Search Report for PCT/KR2017/015485 dated Apr. 11, 2018.
Odian, George, "Principles of Polymerization," 2nd Edition, John Wiley & Sons, Inc. copyright 1981, ISBN: 0-471-05146-2, p. 203.
Schwalm, Reinhold, "UV Coatings: Basics, Recent Developments, and New Applications," Elsevier Science (Dec. 21, 2006), ISBN-10: 0444529799; ISBN-13: 978-0444529794, p. 115.

(Continued)

*Primary Examiner* — Rip A Lee
(74) *Attorney, Agent, or Firm* — Lerner David LLP

(57) ABSTRACT

The present invention relates to a method for preparing superabsorbent polymer. The method for preparing superabsorbent polymer according to the present invention enables providing superabsorbent polymer having excellent absorption ratio, absorption speed and permeability.

8 Claims, 1 Drawing Sheet

(56) References Cited

FOREIGN PATENT DOCUMENTS

| | | | |
|---|---|---|---|
| EP | 3040361 A1 | 7/2016 | |
| EP | 3260485 A1 | 12/2017 | |
| EP | 3279238 A1 | 2/2018 | |
| EP | 3312218 A1 | 4/2018 | |
| JP | H05112654 A | 5/1993 | |
| JP | 2000063527 A | 2/2000 | |
| JP | 2001079829 A | 3/2001 | |
| JP | 3415036 B2 | 6/2003 | |
| JP | 2008526502 A | 7/2008 | |
| JP | 4564284 B2 | 10/2010 | |
| JP | 4866733 B2 | 2/2012 | |
| JP | 2015199958 A | 11/2015 | |
| JP | 2016016667 A | 2/2016 | |
| KR | 100317398 B1 | 11/2002 | |
| KR | 20070007162 A | 1/2007 | |
| KR | 20130093477 A | 8/2013 | |
| KR | 20140094536 A | 7/2014 | |
| KR | 20150067729 A | 6/2015 | |
| KR | 20160048842 A | 5/2016 | |
| KR | 20160048843 A | 5/2016 | |
| KR | 20170002468 A | 1/2017 | |
| KR | 20170005628 A | 1/2017 | |
| WO | 9422502 A1 | 10/1994 | |
| WO | 98051408 A1 | 11/1998 | |
| WO | 2006078046 A2 | 7/2006 | |
| WO | 2011126079 A1 | 10/2011 | |
| WO | 2012174026 A1 | 12/2012 | |
| WO | 2015163510 A1 | 10/2015 | |
| WO | 2015163513 A1 | 10/2015 | |
| WO | WO 2015163513 A1 * | 10/2015 | ................ C08F 2/01 |
| WO | 2016052537 A1 | 4/2016 | |
| WO | 2016158976 A1 | 10/2016 | |

OTHER PUBLICATIONS

Extended European Search Report including Written Opinion for Application No. EP17893930.2. dated May 16, 2019, pp. 1-6.
Third Party Observation in PCT/KR2017/015485 dated Jul. 9, 2019.

* cited by examiner a) 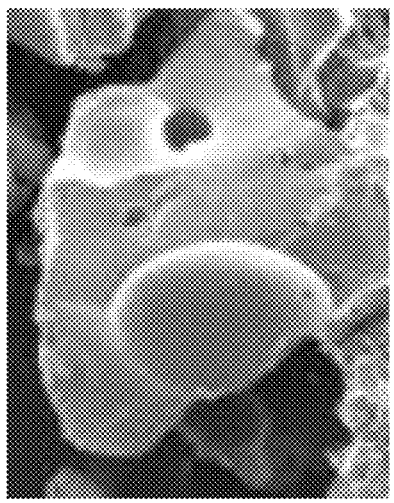
b) 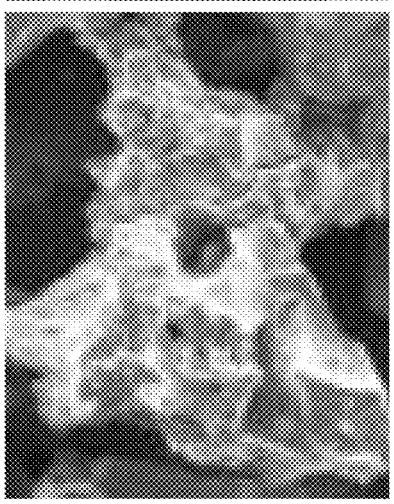
c) 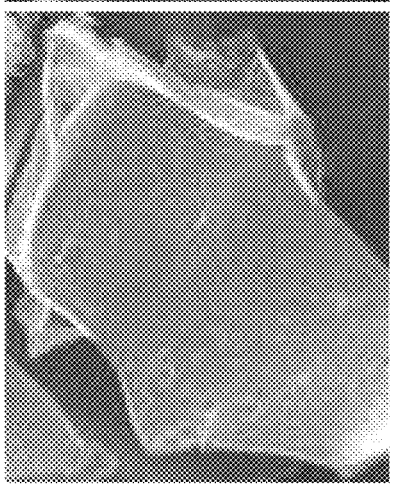

PREPARATION METHOD OF SUPER ABSORBENT POLYMER

CROSS-REFERENCE TO RELATED APPLICATIONS

This application is a national phase entry under 35 U.S.C. § 371 of International Application No. PCT/KR2017/015485, filed Dec. 26, 2017, which claims priority to Korean Patent Application No. 10-2017-0011253, filed Jan. 24, 2017, the disclosures of which are incorporated herein by reference.

TECHNICAL FIELD

The present invention relates to a method for preparing superabsorbent polymer.

BACKGROUND OF ART

Super absorbent polymer (SAP) is synthetic polymer material that can absorb moisture of 500 to 1000 times of self-weight, and is also named as super absorbency material (SAM), absorbent gel material (AGM), etc.

The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, etc.

In most cases, such superabsorbent polymer is being widely used in the field of hygienic goods such as a diaper or sanitary pad, etc., and for such use, it is required to exhibit high absorption power to moisture, etc., and the absorbed moisture should not escape even under external pressure, and besides, it should properly maintain the shape even when it absorbs water and the volume is expanded (swollen), thus exhibiting excellent permeability.

Recently, with the increasing demand for a thin diaper, there is a tendency toward increase in the rate of absorbent polymer in a diaper. Thus, absorbent polymer is required to combine the performance of fiber material of a diaper, and for this, the absorbent polymer should have high absorption speed and permeability as well as high absorption ratio.

During the process of preparing absorbent polymer, in general, a process of chopping hydrogel prepared by the polymerization of the monomers of absorbent polymer is required. The chopping of hydrogel is a process required for preparing superabsorbent polymer in the form of powder or particles, and the process has a large influence on the properties of superabsorbent polymer.

Various studies thereon have been progressed, and for example, Japanese Patent Registration No. 3415036 disclosed a preparation method wherein damage to hydrogel is minimized during chopping, so as to reduce water soluble components inducing deterioration of absorption ratio. However, although the above method enables high absorption ratio, it is insufficient to obtain an absorption speed level recently required in diapers.

For another example, Japanese Patent Registration No. 4866733 disclosed a method of improving permeability and absorption speed of superabsorbent polymer by using 0.2 mol % of an internal crosslinking agent and controlling the hole diameter of a perforated panel of a screw type extruder during chopping of hydrogel. However, although the above method enables high absorption speed and permeability, absorption ratio is deteriorated.

Therefore, there is a continuous demand for the development of technology enabling providing superabsorbent polymer that has further improved absorption ratio, absorption speed and permeability while maintaining excellent basic absorption properties.

DETAILED DESCRIPTION OF THE INVENTION

Technical Problem

It is an object of the present invention to provide a method for preparing superabsorbent polymer capable of preparing superabsorbent polymer that has excellent absorption ratio, absorption speed and permeability, and simultaneously, has excellent properties required for superabsorbent polymer.

Technical Solution

According to the present invention, provided is a method for preparing superabsorbent polymer, comprising the steps of:

conducting crosslinking polymerization of water soluble ethylenically unsaturated monomers having acid groups of which at least a part are neutralized, in the presence of an internal crosslinking agent and an expanding agent to form hydrogel polymer comprising a first crosslinked polymer, chopping the hydrogel polymer, drying the chopped hydrogel polymer, chopping the dried polymer, and surface-modifying the chopped polymer to obtain superabsorbent polymer particles, wherein the step of chopping hydrogel polymer is conducted under chopping index condition of 20 to 35 (/s) according to the following Calculation Formula 1, while pushing the hydrogel polymer to a perforated panel having a plurality of holes using a screw type extruder equipped inside of a cylindrical mill.

Chopping index=$\omega \times (TSC/A)$ tm [Calculation Formula 1]

in the Mathematical Formula 1, $\omega$ is the angular velocity of a screw in the screw type extruder ($2\pi \times N/60$ s), and N is the rotation number (rpm) of the screw.

TSC is the solid content (%) of the hydrogel polymer introduced in the mill, and A is the aperture ratio ($\pi r^2 \times n/\pi R^2$) of the perforated panel, and r is the radius (mm) of the holes formed on the perforated panel, n is the number of the holes formed on the perforated panel, and R is the radius (mm) of the perforated panel.

Hereinafter, a method for preparing superabsorbent polymer according to specific embodiments of the invention will be explained.

Technical terms in the present specification are only for mentioning specific embodiments, and they are not intended to restrict the present invention unless there is a particular mention about them. The singular expressions used herein may include the plural expressions unless they are differently expressed contextually.

The meaning of the terms "comprise" or "include" used in the specification embodies specific characteristics, areas, essences, steps, actions, elements, and/or components, and does not exclude existence or addition of other specific characteristics, areas, essences, steps, actions, elements, components, and/or groups.

As used herein, terms "a first", "a second" and the like are used to distinguish one constructional element from other constructional elements, and are not limited to the ordinal number. For example, within the scope of right of the present invention, a first constructional element may be named as a second constructional element, and similarly, a second constructional element may be named as a first constructional element.

As used herein, the term 'superabsorbent polymer' means polymer that comprises base polymer powder comprising a first crosslinked polymer of water soluble ethylenically unsaturated monomers having acid groups of which at least a part are neutralized; and a surface crosslink layer comprising a second crosslinked polymer formed on the base polymer powder, in which the first crosslinked polymer is additionally crosslinked with a surface crosslinking agent.

Throughout the specification, 'expanded particles' mean particles in which concaves due to expansion occupy ⅓ or more of the particle surface, and 'porous particles' mean particles comprising 3 or more pores of concaves having a depth of 10 μm or more on the surface as shown in FIG. 1(b). And, 'non-shear particles' mean particles excluding the expanded particles and porous particles, which have a smooth surface because deformation of the particles does not occur during the chopping process, as shown in FIG. 1(c).

Meanwhile, as the results of efforts for preparing superabsorbent polymer with excellent properties, the present inventors confirmed that if appropriate shearing force and compressive force are applied during a chopping process simultaneously with introducing expansion during a polymerization process, superabsorbent polymer having high absorption ratio, absorption speed and permeability that was difficult to achieve in the prior art, can be prepared.

Namely, superabsorbent polymer that is prepared by adding appropriate shearing force and compressive force during a chopping process simultaneously with introducing expansion during a polymerization process, comprises expanded particles and porous particles at high rate, thus exhibiting excellent centrifuge retention capacity (CRC), absorbency under pressure (AUP), saline flow conductivity (SFC) and T-20 property.

According to one embodiment of the invention, provided is a method for preparing superabsorbent polymer, comprising the steps of:

1) conducting crosslinking polymerization of water soluble ethylenically unsaturated monomers having acid groups of which at least a part are neutralized, in the presence of an internal crosslinking agent and an expanding agent to form hydrogel polymer comprising a first cross-linked polymer, 2) chopping the hydrogel polymer, 3) drying the chopped hydrogel polymer, 4) chopping the dried polymer, and 5) surface-modifying the chopped polymer to obtain superabsorbent polymer particles, wherein the step of chopping hydrogel polymer is conducted under chopping index condition of 20 to 35 (/s) according to the following Calculation Formula 1, while pushing the hydrogel polymer to a perforated panel having a plurality of holes using a screw type extruder equipped inside of a cylindrical mill.

Chopping index=ω×(TSC/A)  [Calculation Formula 1]

in the Mathematical Formula 1,

ω is the angular velocity of a screw in the screw type extruder (2π×N/60 s), and N is the rotation number (rpm) of the screw.

TSC is the solid content (%) of the hydrogel polymer introduced in the mill, and A is the aperture ratio (πr²×n/πR²) of the perforated panel, and r is the radius (mm) of the holes formed on the perforated panel, n is the number of the holes formed on the perforated panel, and R is the radius (mm) of the perforated panel.

The step 1 is a step of preparing hydrogel polymer, and specifically, a step wherein crosslinking polymerization of water soluble ethylenically unsaturated monomers having acid groups of which at least a part are neutralized is progressed in the presence of an internal crosslinking agent and an expanding agent to form hydrogel polymer comprising a first crosslinked polymer.

The water soluble ethylenically unsaturated monomers may be any monomers commonly used for the preparation of superabsorbent polymer, Specifically, the water soluble ethylenically unsaturated monomers may be a compound represented by the following Chemical Formula 1.

R¹—COOM  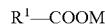  [Chemical Formula 1]

In the Chemical Formula 1,

R¹ is a C2-5 alkyl group comprising an unsaturated bond, and

M¹ is a hydrogen atom, monovalent or divalent metal, an ammonium group or an organic amine salt.

Preferably, the water soluble ethylenically unsaturated monomers may be one or more kinds selected from the group consisting of acrylic acid, methacrylic acid, and monovalent moetal salts and divalent metal salts of these acids, ammonium salt and organic amine salt.

As explained, if acrylic acid or a salt thereof is used as the water soluble ethylenically unsaturated monomers, superabsorbent polymer with improved absorbency can be obtained.

In addition, as the monomers, one or more kinds selected from the group consisting of anionic monomers and salts thereof such as maleic anhydride, fumaric acid, crotonic acid, itaconic acid, 2-acryloylethane sulfonic acid, 2-(meth)acryloylethane sulfonic acid, 2-(meth)acryloyl propane sulfonic acid, or 2-(meth)acrylamido-2-methyl propane sulfonice acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof may be used.

The water soluble ethylenically unsaturated monomer has an acid group, and at least a part of the acid group may be neutralized. Preferably, the monomers partially neutralized with alkali material such as sodium hydroxide, potassium hydroxide, ammonium hydroxide, and the like may be used.

Here, the degree of neutralization of the monomers may be 40 to 95 mol %, or 40 to 80 mol %, or 45 to 75 mol %. The range of the neutralization degree may vary according to the final properties, but if the neutralization degree is too high, neutralized monomers may be precipitated, thus rendering it difficult to smoothly progress polymerization, and to the contrary, if the neutralization degree is too low, absorption force of the polymer may be significantly lowered, and it may exhibit elastic rubber-like property, which is difficult to handle.

And, the monomer composition may further comprise a polymerization initiator commonly used in the preparation of superabsorbent polymer.

As the polymerization initiator, a thermal polymerization initiator or a photopolymerization initiator and the like may be used according to the polymerization method. However, even in the case of photopolymerization, since a certain amount of heat is generated by UV irradiation, etc., and heat is generated to some degree according to the progression of an exothermic polymerization reaction, a thermal polymerization initiator may be additionally included.

As the photopolymerization initiator, one or more selected from the group consisting of benzoin ether, dialkyl acetophenone, hydroxyl alkylketone, phenyl glyoxylate, benzyl dimethyl Ketal, acyl phosphine, and α-aminoketone may be used. Among them, as the acyl phosphine, ude corresponding lucirin TPO, i.e., 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

And, as the thermal polymerization initiator, at least one selected from the group consisting of a persulfate initiator, an azo initiator, hydrogen peroxide, and ascorbic acid may be used.

Specific examples of the persulfate initiator may include sodium persulfate ($Na_2S_2O_8$), potassium persulfate ($K_2S_2O_8$), ammonium persulfate (($NH_4$)$_2S_2O_8$), etc., and, specific examples of the azo initiator may include 2,2-azobis(2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl)propane]dihydrochloride, 4,4-azobis-(4-cyanovalericacid), etc.

More various thermal initiators are described in "Principle of Polymerization (Wiley, 1981)", Odian, page 203, and are not limited to the above described examples.

Such polymerization initiators may be added in the concentration of about 0.001 to 1 wt %, based on the monomer composition. That is, if the concentration of the polymerization initiator is too low, polymerization speed may become slow, and a large quantity of remaining monomers may be extracted in the final product. To the contrary, if the concentration of the polymerization initiator is too high, a polymer chain making up a network may become short, thus increasing water soluble content and decreasing absorbency under pressure, and thus, the properties of the polymer may be deteriorated.

Meanwhile, the polymerization of the monomer composition is conducted in the presence of a crosslinking agent ("internal crosslinking agent") so as to improve the properties of polymer by the polymerization of water soluble ethylenically unsaturated monomers. The crosslinking agent is used to internally crosslink the hydrogel polymer, and is used separately from the "surface crosslinking agent" described below.

As the internal crosslinking agent, any compounds may be used as long as they enable the introduction of crosslink during the polymerization of water soluble ethylenically unsaturated monomers. As non-limiting examples, as the internal crosslinking agent, multifunctional crosslinking agents such as N,N'-methylenebisacrylamide, trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, butyleneglycol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, pentaerythritol tetraacrylate, triallylamine, allyl (meth)acrylate, ethyleneglycol diglycidyl ether, propylene glycol, glycerin, or ethylenecarbonate may be used alone or in combinations.

Such an internal crosslinking agent may be added in the concentration of about 0.001 to 1 wt %, based on the monomer composition. That is, if the concentration of the internal crosslinking agent is too low, the absorption speed of the polymer may decrease, and the gel strength may become weak. To the contrary, if the concentration of the internal crosslinking agent is too high, the absorption force of the polymer may decrease, and thus, it is not preferable as an absorbent.

Meanwhile, the crosslinking polymerization of the monomer composition is conducted in the presence of an expanding agent. The expanding agent may form pores by decomposition during the polymerization and crosslinking reaction of step 1.

As non-limiting examples, the expanding agent may include one or more kinds of compounds selected from the group consisting of sodium bicarbonate, sodium carbonate, potassium bicarbonate, potassium carbonate, calcium bicarbonate, calcium bicarbonate, magnesium bicarbonate, magnesium carbonate, azodicarbonamide (ADCA), dinitroso pentamethylene tetramine (DPT), p,p'-oxybis(benzenesulfonyl hydrazide) (OBSH), p-toluenesulfonyl hydrazide (TSH), sucrose stearate, sucrose palmitate, and sucrose laurate.

It is preferable that the expanding agent exists at 1000 to 3000 ppm in the monomer composition, so as to achieve expansion degree required in the present invention when conducting the step 1. Specifically, the expanding agent may exist in the monomer composition at 1000 ppm or more, or 1100 ppm or more, or 1200 ppm or more, and 3000 ppm or les, or 2500 ppm or less, or 2000 ppm or less.

In addition, the monomer composition may further comprise additives such as a thickener, a plasticizer, a preservation stabilizer, an antioxidant, etc., as necessary.

And, the above explained raw materials such as water soluble ethylenically unsaturated monomers, an internal crosslinking agent, a polymerization initiator, an expanding agent, etc. may be prepared in the form of a solution dissolved in a solvent.

Here, the solvent that can be used is not limited in terms of its construction as long as it can dissolve or disperse the above explained components, and for example, one or more selected from water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, etc. may be used alone or in combination.

A method of forming hydrogel polymer by the polymerization of the monomer composition is not specifically limited in terms of its construction, as long as it is a commonly used polymerization method.

As non-limiting examples, the polymerization method is largely classified into thermal polymerization and photopolymerization according to energy source, and thermal polymerization may be progressed in a reactor equipped with a stirring axis such as a kneader, and photopolymerization may be progressed in a reactor equipped with a movable conveyer belt.

For example, hydrogel polymer may be obtained by progressing thermal polymerization by introducing the monomer composition into a reactor equipped with a stirring axis such as a kneader as explained above, and supplying hot air or heating the reactor. Here, hydrogel polymer discharged to the outlet of the reactor may be in the size of a few centimeters to a few millimeters according to the shape of the stirring axis equipped in the reactor. Specifically, the size of obtained hydrogel polymer may vary according to the concentration of the introduced monomer mixture and the introduction speed, etc, and commonly, hydrogel polymer having (weight average) particle diameter of 2 to 50 mm may be obtained.

And, as another example, in case photopolymerization is progressed in a reactor equipped with a movable conveyer belt as explained above, hydrogel polymer in the form of a sheet may be obtained. Here, the thickness of the polymer sheet may vary according to the concentration of the introduced monomer mixture and the introduction speed, but, commonly, it is preferably controlled to 0.5 to 10 cm, so as to uniformly polymerize the whole sheet and secure production speed, etc.

The moisture content of hydrogel polymer obtained by such a method may be about 40 to about 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to about 180☐ and then maintained at 180☐, and the total drying time is 20 minutes including a temperature raising step of 5 minutes.

Meanwhile, the step 2 is a step of chopping the hydrogel polymer prepared in step 1, wherein the hydrogel polymer is chopped to smaller size (namely, higher surface area), thus increasing the efficiency of subsequent drying. Moreover, in the present invention, the shape of hydrogel polymer may be controlled by controlling chopping conditions, thereby improving the properties of superabsorbent polymer.

Here, used mills are not limited in terms of the constructions, but specifically, one selected from the group consisting of a vertical pulverizer, a turbo cutter, a turbo mill, a rotary cutter mill, a cutter mill, a disc mill, a shred crusher, a crusher, a chopper, a disc cutter may be used, but is not limited thereto.

Meanwhile, when chopping hydrogel polymer, shearing force and compressive force act on the hydrogel polymer, and the present invention is characterized by controlling such chopping conditions. The shearing force is related to a force acting when the hydrogel polymer is pushed with a mill, and the compressive force is related to a force acting when the hydrogle polymer passes through the mill.

Specifically, the step of chopping hydrogel polymer is conducted under chopping index condition of 20 to 35 (/s) according to the following Calculation Formula 1, while pushing the hydrogel polymer to a perforated panel having a plurality of holes using a screw type extruder equipped inside of a cylindrical mill.

$$\text{Chopping index} = \omega \times (TSC/A) \qquad \text{[Calculation Formula 1]}$$

in the Calculation Formula 1, $\omega$ is the angular velocity of a screw in the screw type extruder ($2\pi \times N/60$ s), and N is the rotation number (rpm) of the screw.

TSC is the solid content (%) of the hydrogel polymer introduced in the mill, and A is the aperture ratio ($\pi r^2 \times n/\pi R^2$) of the perforated panel, and r is the radius (mm) of the holes formed on the perforated panel, n is the number of the holes formed on the perforated panel, and R is the radius (mm) of the perforated panel.

Preferably, the chopping of step 2 may be conducted under a chopping index of 20 (/s) or more, or 21 (/s) or more, or 22 (/s) or more, or 23 (/s) or more, or 24 (/s) or more; and 35 (/s) or less, or 32.5 (/s) or less, or 31 (/s) or less, or 30.5 (/s) or less, or 30.1 (/s) or less.

Namely, in order to obtain superabsorbent polymer fulfilling the rate according to shape and the properties required in the present invention, the chopping is preferably conducted under chopping index condition of 20 (/s) or more. However, if the chopping index applied in step 2 is high, although an absorption speed under pressure may be improved, a balance between absorption power and permeability may be deteriorated. Thus, it is preferable for the realization of the above explained properties that the chopping is conducted under chopping index condition of 35 (/s) or less.

By the chopping, various shapes of hydrogel polymer particles are formed. For example, particles formed by the chopping include 'expanded particles' in which concaves due to expansion occupy ⅓ or more of the particle surface as shown in FIG. 1(a); 'porous particles' that comprise three or more pores or concaves having a depth of 10 μm or more on the surface; and 'non-shear particles', which are particles excluding the expanded particles and porous particles, and have a smooth surface because deformation of particles does not occur during the chopping process as shown in FIG. 1(c).

According to the embodiment of the invention, if expansion is introduced in the above explained step of forming hydrogel polymer, the rate of the expanded particles in the chopped hydrogel polymer according to step 2 may be 10% or more, or 10 to 20%, or 10 to 15%, based on the total particle number.

Particularly, according to one embodiment of the invention, if the chopping of hydrogel polymer is conducted under the above descried chopping index condition together with the expansion during the polymerization, the rate of the sum of the expanded particles and porous particles may be 50% or more, or 50 to 70%, or 55 to 70%, based on the total particle number.

According to Examples and Comparative Examples, superabsorbent polymers of Examples prepared under the above described chopping index condition together with the expansion fulfills the rate according to particle shape and the properties required in the present invention, while superabsorbent polymers of Comparative Examples fail to fulfill the rate according to particle shape and the properties required in the present invention.

For example, even if the rate of expanded particles may be 10% or more of the total particle number by introducing expansion during the formation of hydrogel polymer, if chopping index condition is not fulfilled during chopping, the sum of the expanded particles and porous particles may be less than 50% of the total particle number. As such, if the rate of expanded particles, and the rate of the sum of expanded particles and porous particles do not fulfill the above explained rages, it is difficult to fulfill the properties required in the present invention.

The chopping of hydrogel polymer may be conducted such that the particle diameter of hydrogel polymer may become 0.1 mm to 10 mm. Namely, it is preferable that the hydrogel polymer is chopped to particles of 10 mm or less so as to increase the efficiency of drying. However, since agglomeration of particles may be generated by excessive chopping, it is preferable that the hydrogel polymer is chopped to particles of 0.1 mm or more.

And, since the chopping of hydrogel polymer is conducted in the state of high moisture content, hydrogel polymer may be adhered to the surface of a mill. In order to minimize such phenomenon, steam, water, surfactant, an anti-agglomeration agent (for example, clay, silica, etc.); a persulfate-based initiator, an azo-based initiator, hydrogen peroxide, a thermal polymerization initiator, an epoxy-based crosslinking agent, a diol-based crosslinking agent, a crosslinking agent including bifunctional or trifunctional or multifunctional acrylate, a monofunctional crosslinking agent including a hydroxide group, etc. may be added to hydrogel polymer, as necessary.

The step 3 is a step of drying the hydrogel polymer chopped in step 2.

The drying may be conducted at 120 to 250° C., preferably 140 to 200° C., more preferably 150 to 190° C. Here, the drying temperature may be defined as the temperature of heating medium supplied for drying, or the temperature inside of a drying reactor including heating medium and polymer during a drying process. If the drying temperature is low and the drying time lengthens, process efficiency may be lowered, and in order to prevent this, it is preferable that the drying temperature is 120° C. or more. And, if the drying temperature is high beyond necessary, the surface of hydrogel polymer may be excessively dried, thus generating a lot of fine particles during the subsequent chopping process, and the properties of the final polymer may be deteriorated, and in order to prevent this, it is preferable that the drying temperature is 250° C. or less.

Here, although a drying time in the drying step is not specifically limited, it may be controlled to 20 to 90 minutes under the above drying temperature, considering process efficiency and the properties of polymer, etc.

The drying may be achieved using common media, and for example, it may be conducted through hot wind supply, infrared ray irradiation, ultrahigh frequency wave irradiation, or UV irradiation, etc.

And, it is preferable that the drying is conducted such that the dried polymer may have a moisture content of about 0.1 to 10 wt %. Namely, if the moisture content of dried polymer is less than 0.1 wt %, manufacture cost increase and degradation of crosslinked polymer may occur due to excessive drying. And, if the moisture content of dried polymer is greater than 10 wt %, faulty may be generated in the subsequent process.

The step 4 is a step of chopping the polymer dried in step 3, and it is to optimize a surface area. The chopping may be conducted such that the particle diameter of chopped polymer may become 150 to 850 μm.

Here, commonly used mills such as a pin mill, a hammer mill, a screw mill, a roll mill, a disc mill, or a jog mill, etc. may be used.

And, in order to manage the properties of the finally productized superabsorbent polymer, a step of selectively sieving particles having a particle diameter of 150 to 850 μm in the polymer particles obtained through the chopping step, may be further conducted.

Meanwhile, through the sieving, polymer particles having a particle diameter less than 150 μm may be assembled with a solvent (for example, water) that can be used in step 1 to prepare reassembled fine particles. The reassembled fine particles may be added to the hydrogel polymer of step 2. Specifically, the addition of the reassembled fine particles may be conducted immediately before, during, or after the chopping of step 2. The amount of the reassembled fine particles added may be preferably 30 wt % or less, based on the hydrogel polymer of step 2.

The step 5 is a step of surface-modifying the polymer chopped in step 4.

The surface modification induces a crosslinking reaction on the surface of the chopped polymer in the presence of a second crosslinking agent (surface crosslinking agent), and through the surface modification, a surface modified layer (surface crosslink layer) is formed on the surface of the chopped polymer particles.

The surface modification may be conducted by a common method for increasing the crosslinking density of a polymer particle surface, and for example, it may be conducted by mixing a solution comprising a second crosslinking agent (surface crosslinking agent) and the chopped polymer to progress a crosslinking reaction.

Here, the second crosslinking agent is a compound that can be reacted with the functional group of the polymer, and C2-5 alkylene carbonate is preferable. More preferably, as the second crosslinking agent, ethylene carbonate may be used. And, in addition to the second crosslinking agent, porous silica or clay, etc. may be further included. And, in order to control the penetration speed and depth of the second crosslinking agent, an acid compound or polymer, etc. may be further added, as necessary.

Here, the content of the second crosslinking agent may be appropriately controlled according to the kind of the crosslinking agent or reaction conditions, etc., and preferably, it may be controlled to 0.001 to 5 parts by weight, based on 100 parts by weight of the chopped polymer. If the content of the second crosslinking agent is too low, surface modification may not be properly achieved, thus deteriorating the properties of the final polymer. To the contrary, if an excessive amount of the second crosslinking agent is used, the absorption force of polymer may be lowered on the contrary, due to excessive surface crosslinking reaction.

Meanwhile, the surface modification step may be conducted by common methods such as putting the second crosslinking agent and chopped polymer in a reactor to mix them, spraying the second crosslinking agent to chopped polymer, continuously feeding chopped polymer and the second crosslinking agent to a mix continuously operated, and the like.

And, when adding the second crosslinking agent, water may be additionally added. As such, the addition of water together with the second crosslinking agent may induce uniform dispersion of the second crosslinking agent, prevent the agglomeration of polymer particles, and further optimize the penetration depth of the second crosslinking agent to polymer particles. Considering such objects and effects, the content of water added together with the second crosslinking agent may be controlled to 0.5 to 10 parts by weight, based on 100 parts by weight of the chopped polymer.

And, the surface modification step may be progressed at a temperature of 100 to 250° C. And, the surface modification may be progressed for 1 minute to 120 minutes, preferably 1 minute to 100 minutes, more preferably, 10 minutes to 80 minutes. Namely, in order to induce minimum surface crosslinking reaction, and simultaneously, prevent damage to polymer particles and the resulting property deterioration by excessive reactions, the surface modification step may be conducted under the above explained conditions.

Meanwhile, according to the embodiment of the invention, superabsorbent polymer prepared according to the above explained method is provided.

The superabsorbent polymer comprises base polymer powder comprising a first crosslinked polymer of water soluble ethylenically unsaturated monomers having acid groups of which at least a part are neutralized; and a surface crosslink layer that is formed on the base polymer powder, and comprises a second crosslinked polymer in which the first crosslinked polymer is additionally crosslinked with a surface crosslinking agent.

The superabsorbent polymer is obtained as particles having a particle diamere of 150 to 850 μm.

Particularly, since the superabsorbent polymer is prepared by the above explained method, it has excellent absorption ratio, absorption speed and permeability, which may be represented by centrifuge retention capacity (CRC), absorbency under pressuer (AUP), saline flow conductivity (SFC), T-20, etc.

Specifically, centrifuge retention capacity (CRC) to a saline solution (0.9 wt % sodium chloride aqueous solution) for 30 minutes may be 26 g/g or more, preferably 26.5 g/g or more, or 27 g/g or more, or 27.4 g/g or more. The higher CRC is more excellent, and thus, the upper limit is not limited, but for example, the CRC of the superabsorbent polymer may be 30 g/g or less, or 29.5 g/g or less, or 29 g/g or less, or 28.5 g/g or less.

The CRC of the superabsorbent polymer may be measured according to European Disposables and Nonwovens Association (EDANA) Standard EDANA WSP 241.3, and it may be calculated according to the Calculation Formula A described in the Experimental Example.

And, absorbency under pressure (AUP) under 0.7 psi to a saline solution (0.9 wt % sodium chloride aqueous solution) for 1 hour may be 21 g/g or more, preferably 22 g/g or more, or 23 g/g or more, or 23.4 g/g or more. The higher AUP value is more excellent, and thus, the upper limit is not limited, but for example, the AUP of the superabsorbent polymer may be 29 g/g or less, or 28 g/g or less, or 27 g/g or less.

The AUP of the superabsorbent polymer may be measured according to European Disposables and Nonwovens Association Standard EDANA WSP 242.3, and it may be calculated according to the Calculation Formula B described in the Experimental Example.

And, saline flow conductivity (SFC) for a saline solution (0.685 wt % sodium chloride aqueous solution) may be 35 ($\cdot 10^{-7}$ cm3·s/g) or more, preferably 37 or more. The higher SFC is more excellent, and thus, the upper limit is not limited, but for example, the SFC of the superabsorbent polymer may be 100 or less, or 90 or less, or 80 or less.

The SFC may be measured and calculated according to methods well known to a person having ordinary knowledge, for example, a method disclosed in column 54 to column 59 of U.S. Pat. No. 5,562,646.

And, T-20 indicating a time taken for 1 g of superabsorbent polymer to absorb 20 g of an aqueous solution of 0.01 wt % C12-14 alcohol ethoxylate and 0.9 wt % sodium chloride may be 190 seconds or less, preferably 180 seconds or less, or 170 seconds or less. The smaller T-20 is more excellent, and thus, the lower limit is not limited, but for example, the T-20 of the superabsorbent polymer may be 80 seconds or more, or 90 seconds or more, or 100 seconds or more, or 110 seconds or more.

The T-20 of the superabsorbent polymer may be calculated and measured as a time (seconds) taken for 1 g of superabsorbent polymer to absorb 20 g of an aqueous solution that is prepared by dissolving 9 g of sodium chloride and 0.1 g of Lorodac (main ingredient: linear C12-14 alcohol ethoxylate, CAS #68439-50-9) in 1 L of distilled water. The specific measurement method of T-20 is described in detail in pages 13 to 18 of European Patent Publication No. 2535027.

Advantageous Effects

The preparation method of superabsorbent polymer according to the present invention enables providing superabsorbent polymer with excellent absorption ratio, absorption speed and permeability. Such superabsorbent polymer may be suitably used as hygienic goods such as a diaper, etc., particularly, for ultra thin hygienic goods.

BRIEF DESCRIPTION OF THE DRAWINGS

FIG. 1 shows the SEM images of expanded particles in which concaves due to expansion occupy ⅓ or more of the particle surface [FIG. 1(a)], porous particles that comprise three or more pores or concaves having a depth of 10 μm or more on the surface [FIG. 1(b), and non-shear particles that have a smooth surface because deformation of particles does not occur during the chopping process [FIG. 1(c)] in the polymer particles prepared according to Example 1 of the present invention.

DETAILED DESCRIPTION OF THE EMBODIMENTS

Hereinafter, the actions and the effects of the invention will be explained in detail through the specific examples. However, these examples are presented only as the illustrations of the invention, and the scope of the right of the invention is not limited thereby.

EXAMPLES AND COMPARATIVE EXAMPLES

As an apparatus for preparing superabsorbent polymer, an apparatus for continuous preparation consisting of a polymerization process, a hydrogel chopping process, a drying process, a chopping process, a sieving process, a surface crosslinking process, a cooling process, a sieving process, and transport processes connecting each process, was used.

(Step 1)

100 parts by weight of acrylic acid were mixed with 0.4 parts by weight of polyethyleneglycol diacrylate (weight average molecular weight: ~500 g/mol) and 0.1 parts by weight of hexanediol diacrylate as internal crosslinking agents, and 0.01 parts by weight of IRGACURE 819 as a photoinitiator to prepare a monomer solution. Subsequently, while continuously feeding the monomer solution with a metering pump, 160 parts by weight of 24 wt % sodium hydroxide aqueous solution were continuously line mixed to prepare a monomer aqueous solution. Here, it was confirmed that the temperature of the monomer aqueous solution raised to about 72° C. or more by neutralization heat, and then, waited until the temperature is cooled to 40° C.

When the temperature was cooled to 40° C., solid sodium bicarbonate, an expanding agent, was added to the monomer aqueous solution in the content described in the following Table 1, and simultaneously, 6 parts by weight of 2 wt % sodium persulfate aqueous solution was added.

The solution was poured into a tray in the form of Vat (tray, width 15 cm×length 15 cm) installed in a square polymerization reactor, on which a light irradiation device was mounted, and of which inside was preheated to 80° C., and light irradiation was conducted to photoinitiate. It was confirmed that gel was generated from the surface about 25 seconds after the photoinitiation, and that polymerization occurred simultaneously with expansion after about 50 seconds, and hydrogel polymer in the form of a sheet was obtained by additional reaction for 3 minutes.

(Step 2)

The hydrogel polymer in the form of a sheet obtained in step 1 was cut into a size of 3 cm×3 cm, and then, chopped under chopping index condition as shown in the following Calculation Formula 1 and Table 1, while pushing the hydrogel polymer to a perforated panel having a plurality of holes using a screw type extruder equipped inside of a cylindrical mill.

Chopping index$(C.I.) = \omega \times (TSC/A)$     [Calculation Formula 1]

in the Calculation Formula 1, $\omega$ is the angular velocity of a screw in the screw type extruder ($2\pi \times N/60$ s), and N is the rotation number (rpm) of the screw.

TSC is the solid content (%) of the hydrogel polymer introduced in the mill, and A is the aperture ratio ($\pi r^2 \times n/\pi R^2$) of the perforated panel, and r is the radius (mm) of the holes formed on the perforated panel, n is the number of the holes formed on the perforated panel, and R is the radius (mm) of the perforated panel.

TABLE 1

| | Expanding agent (ppm) | N (rpm) | TSC | r (mm) | R (mm) | n | C.I. (/s) |
|---|---|---|---|---|---|---|---|
| Example 1 | 2000 | 180 | 0.44 | 4.5 | 42 | 24 | 30.1 |
| Example 2 | 1600 | 180 | 0.44 | 4.5 | 42 | 24 | 30.1 |
| Example 3 | 1400 | 180 | 0.44 | 5.0 | 42 | 24 | 24.4 |
| Example 4 | 1200 | 180 | 0.44 | 5.0 | 42 | 24 | 24.4 |
| Comparative Example 1 | 0 | 105 | 0.44 | 5.0 | 42 | 24 | 14.2 |
| Comparative Example 2 | 0 | 180 | 0.44 | 4.5 | 42 | 24 | 30.1 |
| Comparative Example 3 | 2000 | 105 | 0.44 | 4.5 | 42 | 24 | 17.6 |

(Step 3)

Subsequently, the hydrogel polymer chopped in step 2 was dried in a drier capable of transferring air volume up and down. Hot air of 180° C. was allowed to flow from the lower side to the upper side for 15 minutes such that the moisture content of dried powder became about 2% or less, and then, it was allowed to flow again from the upper side to the lower side for 15 minutes, thus uniformly drying the hydrogel polymer.

(Step 4)

The polymer dried in step 3 was chopped with a mill, and then, sieved to obtain base polymer of 150 to 850 μm.

(Step 5)

100 parts by weight of the base polymer prepared in step 4 were mixed with 3 parts by weight of water, 3 parts by weight of methanol, and 0.5 parts by weight of ethylene carbonate, and then, surface crosslinking was conducted at 180° C. for 40 minutes. And, the obtained product was cooled, and then, sieved to obtain surface crosslinked superabsorbent polymer particles with a particle diameter of 150 to 850 μm.

EXPERIMENTAL EXAMPLE

The properties of each superabsorbent polymer prepared in Examples and Comparative Examples were measured and evaluated as follows.

(1) A Rate According to Particle Shape

The superabsorbent polymer particles were observed with scanning electron microscope (SEM), to calculate the rate of expanded particles in which concaves due to expansion occupy ⅓ or more of the particle surface (classified as porous particles if the rate is less than ⅓), porous particles that comprise three or more pores or concaves having a depth of 10 μm or more on the surface, and non-shear particles that have a smooth surface because deformation of particles does not occur during the chopping process, in the total particles.

Among them, the SEM images of the expanded particles [FIG. 1(a)], the porous particles [FIG. 1(b) and the non-shear particles [FIG. 1(c)] in the superabsorbent polymer particles according to Example 1 were shown in FIG. 1.

(2) Centrifuge Retention Capacity (CRC)

A centrifuge retention capacity (CRC) by the absorption scale under no load was measured according to European Disposables and Nonwovens Association, (EDANA) Standard EDANA WSP 241.3

Specifically, $W_0$ (g, about 0.2 g) of the superabsorbent polymer was uniformly put in an envelope made of nonwoven fabric and sealed, and then, immersed in a 0.9 wt % sodium chloride saline solution at room temperature. After 30 minutes, the envelope was drained at 250 G for 3 minutes using a centrifuge, and then, the mass $W_2$(g) of the envelope was measured. And, after the same operation without using superabsorbent polymer, the mass $W_1$(g) at that time was measured. Using the obtained masses, CRC (g/g) was calculated according to the following Calculation Formula A, thus confirming centrifuge retention capacity.

$CRC(g/g) = \{[W_2(g) - W_1(g) - W_0(g)]/W_0(g)\}$     [Calculation Formula A]

(3) Absorbing Under Pressure (AUP)

Absorbing under pressure was measured according to European Disposables and Nonwovens Association Standard EDANA WSP 242.3.

Specifically, on the bottom of plastic cylinder of 60 mm inner diameter, stainless 400 mesh wire netting was installed. Superabsorbent polymer $W_0$ (g, 0.90 g) was uniformly sprayed onto the wire netting under temperature of 23±2° C. and 45% humidity, and a piston capable of uniformly giving 4.83 kPa (0.7 psi) load thereon has an outer diameter slightly less than 60 mm and does not have a gap with the inner wall of cylinder, and the upward and downward movement is not hindered.

At this time, the weight $W_3$(g) of the apparatus was measured. In the inner side of a petri dish of 150 mm diameter, a glass filter of 125 mm diameter and 5 mm thickness was placed, and a saline solution consisting of 0.90 wt % sodium chloride was placed to the same level as the upper side of the glass filter. One filter paper of 120 mm diameter was loaded thereon. The measuring apparatus was loaded on the filter paper, and the liquid was absorbed under load for 1 hour. After 1 hour, the measuring apparatus was lifted, and the weight $W_4(g)$ was measured. Using each weight obtained above, AUL (g/g) was calculated according to the following Calculation Formula B, thus confirming absorbency under pressure.

$$AUP(g/g)=[W_4(g)-W_3(g)]/W_0(g) \qquad \text{[Calculation Formula B]}$$

(4) Saline Flow Conductivity (SFC)

A saline flow conductivity was measured and calculated according to the method disclosed in column 54 to column 59 of U.S. Pat. No. 5,562,646.

(5) T-20

An aqueous solution was prepared by dissolving 9 g of sodium chloride and 0.1 g of Lorodac (main ingredient: linear C12-14 alcohol ethoxylate, CAS #68439-50-9) in 1 L of distilled water, and T-20 was calculated as a time (seconds) taken for 1 g of superabsorbent polymer to absorb 20 g of the aqueous solution. The specific measurement method of T-20 is describe in detail in pages 13 to 18 of European Patent Publication No. 2535027.

TABLE 2

| | Expanded particles(%) | Porous particles(%) | Non-shear particles(%) |
|---|---|---|---|
| Example 1 | 11 | 53 | 36 |
| Example 2 | 12 | 55 | 33 |
| Example 3 | 14 | 42 | 44 |
| Example 4 | 10 | 46 | 44 |
| Comparative Example 1 | 2 | 20 | 78 |
| Comparative Example 2 | 1 | 34 | 65 |
| Comparative Example 3 | 15 | 22 | 63 |

TABLE 3

| | CRC (g/g) | AUP (g/g) | SFC ($\cdot 10^{-7} cm^3 \cdot s/g$) | T-20 (sec) |
|---|---|---|---|---|
| Example 1 | 28.1 | 25.6 | 60 | 116 |
| Example 2 | 28.5 | 26.1 | 55 | 132 |
| Example 3 | 28.1 | 23.4 | 37 | 170 |
| Example 4 | 27.4 | 24.3 | 41 | 165 |
| Comparative Example 1 | 29.5 | 23.5 | 30 | 240 |
| Comparative Example 2 | 27.0 | 23.8 | 30 | 180 |
| Comparative Example 3 | 25.8 | 24.3 | 70 | 114 |

Referring to Tables 1 to 3, since the superabsorbent polymers according to Examples 1 to 3 were obtained through the polymerization process introducing expansion and the hydrogel chopping process under appropriate chopping index, the rate of the expanded particles was 10% or more of the total particle number, and the rate of the sum of the expanded particles and porous particles was 50% or more of the total particle number.

To the contrary, in the superabsorbent polymer of Comparative Examples 1 and 2, the rate of non-shear particles was as high as 65% or more of the total particle number, and the rates of the expanded particles and porous particles were low. In the superabsorbent polymer of Comparative Example 3, the rate of the expanded particles was as high as 15% of the total particle number, but the rate of the porous particles was as low as 22%.

And, compared to the superabsorbent polymers according to Comparative Examples 1 to 3, the superabsorbent polymers according to Examples 1 to 3 had equivalent absorbing under pressure (AUP), but exhibited excellent centrifuge retention capacity (CRC), saline flow conductivity (SFC) and T-20 property.

The invention claimed is:

1. A method for preparing superabsorbent polymer comprising:
    conducting crosslinking polymerization of a monomer composition including water soluble ethylenically unsaturated monomers having acid groups of which at least a part are neutralized, in the presence of an internal crosslinking agent and an expanding agent to form a hydrogel polymer comprising a first crosslinked polymer,
    chopping the hydrogel polymer to produce a chopped hydrogel polymer,
    drying the chopped hydrogel polymer to produce a dried polymer,
    chopping the dried polymer to produce a chopped polymer, and
    surface-modifying the chopped polymer to obtain the superabsorbent polymer,
    wherein the chopping the hydrogel polymer is conducted under a chopping index condition of 20 to 35 (/s) according to the following Mathematical Formula 1, while pushing the hydrogel polymer into a perforated panel having a plurality of holes using a screw extruder equipped inside of a cylindrical mill;

$$\text{Chopping index}=\omega \times (TSC/A) \qquad \text{[Mathematical Formula 1]}$$

in the Mathematical Formula 1,
    $\omega$ is an angular velocity of a screw in the screw extruder ($2\pi \times N/60$ s), and N is a rotation number (rpm) of the screw,
    TSC is a solid content (%) of the hydrogel polymer introduced into the cylindrical mill, and
    A is an aperture ratio ($\pi r^2 \times n/\pi R^2$) of the perforated panel, and r is a radius (mm) of the plurality of holes formed on the perforated panel, n is a number of holes formed on the perforated panel, and R is a radius (mm) of the perforated panel,
    wherein in the superabsorbent polymer, a rate of expanded particles in which concaves due to expansion occupy ⅓ or more of a particle surface, is 10% or more of a total particle number.

2. The method according to claim 1, wherein the expanding agent is present in the monomer composition at 1000 to 3000 ppm.

3. The method according to claim 1, wherein in the superabsorbent polymer particles, a rate of a sum of expanded particles in which concaves due to expansion occupy ⅓ or more of a particle surface, and porous particles comprising three or more pores or concaves having a depth of 10 μm or more on a surface is 50% or more of a total particle number.

4. The method according to claim 1, wherein in the superabsorbent polymer particles, centrifuge retention capacity (CRC) to a saline solution (0.9 wt % sodium chloride aqueous solution) for 30 minutes is 26 g/g or more,
    absorbency under pressure (AUP) under 0.7 psi to a saline solution (0.9 wt % sodium chloride aqueous solution) for 1 hour is 21 g/g or more,
    saline flow conductivity (SFC) for a saline solution (0.685 wt % sodium chloride aqueous solution) is 35 ($\cdot 10^{-7}$ cm$^3$ s/g) or more, and T-20 indicating a time taken for 1 g of superabsorbent polymer to absorb 20 g of an aqueous solution of 0.01 wt % C12-14 alcohol ethoxylate and 0.9 wt % sodium chloride is 190 seconds or less.

5. The method according to claim 1, wherein the internal crosslinking agent comprises one or more compounds selected from the group consisting of N,N'-methylenebisacrylamide, trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, butyleneglycol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, pentaerythritol tetraacrylate, triallylamine, allyl (meth)acrylate, ethyleneglycol diglycidyl ether, propylene glycol, glycerin, and ethylenecarbonate.

6. The method according to claim 1, wherein the expanding agent comprises one or more compounds selected from the group consisting of sodium bicarbonate, sodium carbonate, potassium bicarbonate, potassium carbonate, calcium bicarbonate, calcium bicarbonate, magnesium bicarbonate, magnesium carbonate, azodicarbonamide (ADCA), dinitroso pentamethylene tetramine (DPT), p,p'-oxybis(benzenesulfonyl hydrazide) (OBSH), p-toluenesulfonyl hydrazide (TSH), sucrose stearate, sucrose palmitate, and sucrose laurate.

7. The method according to claim 1, wherein the water soluble ethylenically unsaturated monomers comprise one or more compounds selected from the group consisting of anionic monomers selected from acrylic acid, methacrylic acid, maleic anhydride, fumaric acid, crotonic acid, itaconic acid, 2-acryloylethane sulfonic acid, 2-(meth)acryloylethane sulfonic acid, 2-(meth)acryloyl propane sulfonic acid, or 2-(meth)acrylamido-2-methyl propane sulfonic acid, and salts thereof; non-ionic hydrophilic group containing monomers selected from (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers selected from (N,N)-dimethylaminoethyl (meth)acrylate, (N,N)-dimethylaminopropyl (meth)acrylamide, or quaternized products thereof.

8. The method according to claim 1, wherein the superabsorbent polymer has a particle diameter of 150 to 850 μm.

* * * * *